United States Patent [19]
Prigent

[11] Patent Number: 5,641,971
[45] Date of Patent: Jun. 24, 1997

[54] METHOD AND DEVICE FOR COUNTING AND CHARACTERIZING DEFECTS ON A PHOTOGRAPHIC SUPPORT

[75] Inventor: Thierry Prigent, Sainte-Helene, France

[73] Assignee: Eastman Kodak Company, Rochester, N.Y.

[21] Appl. No.: 488,995

[22] Filed: Jun. 8, 1995

[30] Foreign Application Priority Data

Jun. 15, 1994 [FR] France .................................. 9407601

[51] Int. Cl.⁶ ............................................... G01N 21/86
[52] U.S. Cl. ........................ 250/559.02; 250/559.03; 250/559.46; 356/430
[58] Field of Search .................. 250/559.02, 559.03, 250/559.05, 559.45, 559.46; 377/3, 6, 12; 382/149, 145; 356/430, 237

[56] References Cited

U.S. PATENT DOCUMENTS

| | | | |
|---|---|---|---|
| 3,599,223 | 8/1971 | Bridenbaugh et al. | 356/430 |
| 4,252,053 | 5/1979 | Menary | 356/430 |
| 4,417,149 | 11/1983 | Takeuchi et al. | 250/559.45 |
| 4,764,969 | 8/1988 | Ohtombe et al. | 382/8 |
| 5,278,411 | 1/1994 | Popil et al. | 250/330 |
| 5,424,555 | 6/1995 | Kimura et al. | 250/559.02 |

FOREIGN PATENT DOCUMENTS

| | | |
|---|---|---|
| 1220275 | 4/1987 | Canada . |
| 61-245007 | 10/1986 | Japan . |
| 2-040541 | 2/1990 | Japan . |

OTHER PUBLICATIONS

*Journal of Imaging Science and Technology*, vol. 37, No. 2, "Application of Digital Image Analysis Techniques to Photographic Film Defect Test Method Development", Mar./Apr. 1993, Edward Cohen and Ronald Grotovsky, pp. 133–148.

Primary Examiner—Que Le
Attorney, Agent, or Firm—Clyde E. Bailey, Sr.; Charles E. Snee, III

[57] ABSTRACT

A method and device for counting and characterizing defects on a photographic support includes inspecting the support with an optical density measuring device. The defects present on the support are then detected, counted and then characterized.

5 Claims, 1 Drawing Sheet

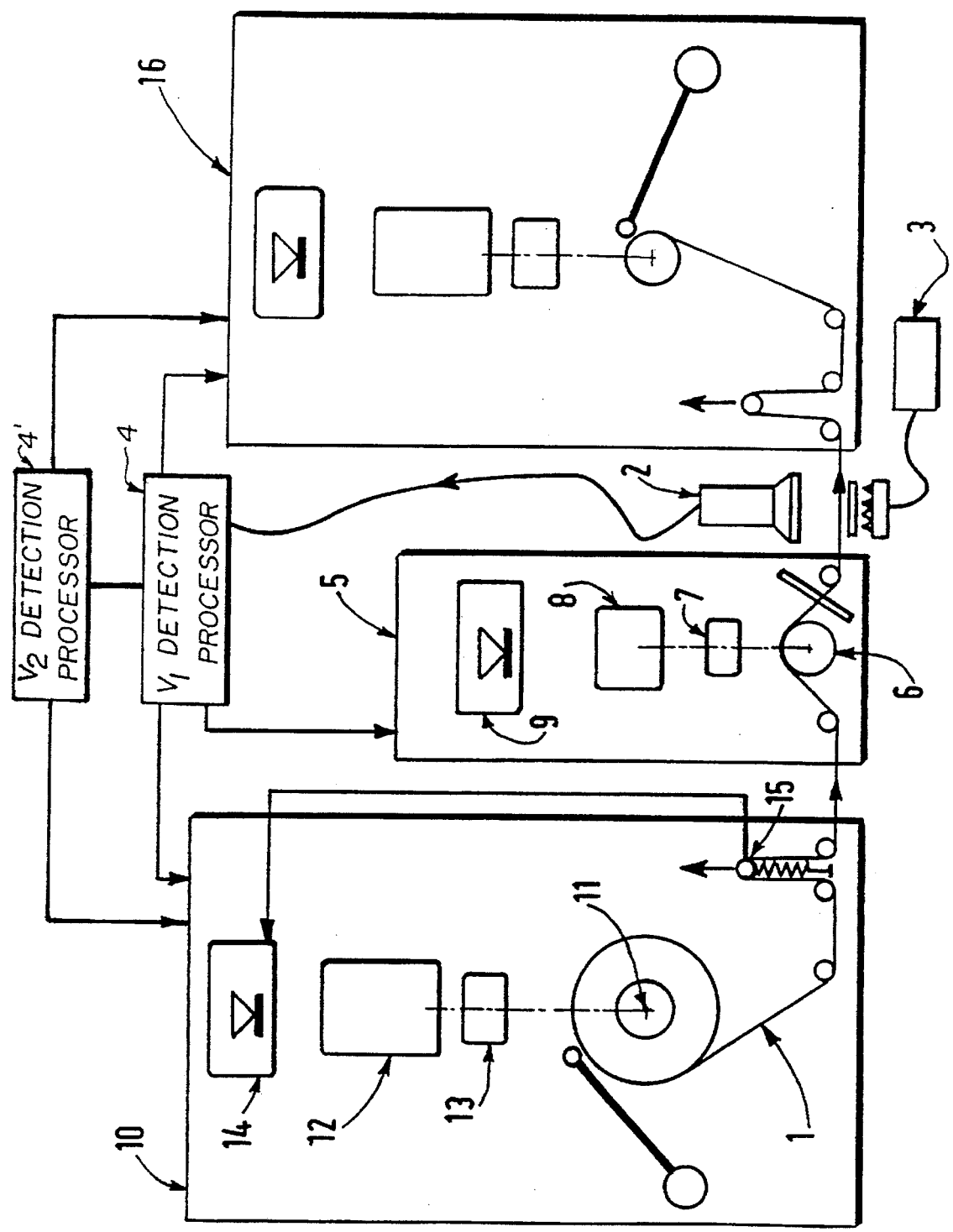

METHOD AND DEVICE FOR COUNTING AND CHARACTERIZING DEFECTS ON A PHOTOGRAPHIC SUPPORT

FIELD OF THE INVENTION

The present invention concerns a method and a device for counting and characterizing defects on a photographic support. The method preferably concerns a support in the form of a photographic film in strip form.

BACKGROUND OF THE INVENTION

In the photographic industry, one of the parameters affecting the quality of the film is related to the presence of physical defects on the film which may substantially affect the quality of the use which the user may make of the film.

Within the scope of the present invention, the term defect designates on the one hand any objects or particles which may be present on the surface of the photographic film. An example of this would be any dust such as might result from cutting the film, or atmospheric dust which may be deposited on the film by electrostatic attraction or when the film passes over rollers or suitable transport devices. It may also be a case of particles or pieces of film (or of components of the film) torn off the surface of the film and remaining on the surface of the film, or resulting from cutting the film. Moreover, the term defect also designates structural defects of the surface due, for example, to abrasion, or to what is generally known as "exposure stoppage". In fact, these are optical density defects after development due to local inhomogeneity of the film or to an obstacle interposed during the exposure of the film, between the uniform greying light source and the film.

Since the number and nature of such defects are representative of the quality of the film manufacturing process, it has seemed desirable to develop a method and an apparatus enabling the defects present on such a photographic support to be counted in a simple and reliable manner. It is also important to characterize the defects detected in order to identify any weaknesses in the process used for manufacturing the photographic support in question.

Traditionally, the counting and characterization of the defects on a photographic support were carried out manually by an operator after greying and development of the film examined. Such an approach has the drawback of being tedious, of low reproducibility and imprecise.

According to another known approach, a device of the scanner type is used, utilizing a light beam scanning the surface of the film passing at a constant speed in front of the said scanner. This method, apart from the fact that it operates in analog fashion, has the drawback of not affording sufficient resolution because of the size of the light spot. Typically, the size of such a spot is approximately 1 $mm^2$. In addition, this does not allow correct use for film samples of small dimensions.

SUMMARY OF THE INVENTION

One of the objects of the present invention is therefore to provide a method and device which do not have the drawbacks discussed above.

Other objects of the present invention will emerge in detail during the following description.

These objects are achieved by providing a method for counting and characterizing defects on a photographic support in which the support is caused to pass in front of an optical density measuring device and in which the density values given by the said device are analyzed for the purpose of detecting, counting and characterizing the defects, the said method being characterized in that the defects are detected for a first speed V1 at which the support passes and in that the data necessary for the counting and characterization of the defects thus detected are captured and stored for a second speed V2 at which the support passes, less than V1.

According to a first embodiment, the method according to the invention comprises the following steps:

a) causing the support to pass at a first speed V1 in front of a device for measuring the optical density of the said support;

b) digitizing the information relating to the optical density of the support generated by the said device;

c) detecting any change in density, the magnitude of which is representative of the presence of at least one defect;

d) when such a change is detected, stopping the movement of the support;

e) moving the support with respect to the measuring means so that the said measuring means are facing an area of the support situated upstream of the first defect detected;

f) causing the support to pass in front of the said measuring means at a second speed V2, less than the first speed V1, until the said measuring means are facing an area of the support situated downstream of the last defect detected;

g) storing the information relating to the optical density of the said support during the passage of the support at the said second speed V2;

h) repeating steps a) to g) for the remainder of the support;

i) processing the information thus stored during the periods of passage at speed V2, so as to count and characterize the defects detected.

According to the present invention, an apparatus is also produced for counting and characterizing defects on a photographic support, comprising:

a) an optical density measuring device in front of which the support is caused to pass;

b) means for analyzing the density values given by the said device, for the purpose of detecting, counting and characterizing the defects;

the said apparatus being characterizing in that it comprises means for selectively causing the support to pass at a first speed V1 for the detection of the defects and at a second speed V2, less than V1, for the capturing and storage of the density values required for the counting and characterization of the defects thus detected.

Advantageously, the device comprises:

a) means for causing the support to pass at a first speed V1 in front of a device for measuring the optical density of the said support;

b) means for digitizing the information relating to the optical density of the support generated by the said device;

c) means for detecting any change in density, the magnitude of which is representative of the presence of at least one defect;

d) means for, when such a change is detected, stopping the passage of the support and moving it with respect to the measuring means so that the said measuring means are facing an area of the support situated upstream of the first defect detected;

e) means for causing the support to pass in front of the said measuring means at a second speed V2, less than the first speed V1, until the said measuring means are facing an area of the support situated downstream of the last defect detected;

f) means for storing the information relating to the optical density of the said support during the passage of the support at the said second speed V2;

g) means for processing the information thus stored so as to count and characterize the defects detected.

BRIEF DESCRIPTION OF THE DRAWINGS

The detailed description which follows will be given with reference to the drawing in which:

The FIGURE shows diagrammatically an embodiment of the device for implementing the method according to the present invention.

DETAILED DESCRIPTION

According to the embodiment shown in the FIGURE, the film 1 passes in front of an optical density measuring device. By way of example, this may be a linear CCD camera 2. Preferably, in order to be in a position to detect defects of a size which may be as little as 10 µm, a camera offering a resolution of 11.23 µm is used. Even smaller defect sizes may be detected by using suitable optical devices between the camera and film. Such devices modify the enlargement of the image observed by the camera. Such optical arrangements are well known to experts and consequently do not require any additional description.

The camera 2 observes the image of the film 1 illuminated by a light source 3. By way of example, a halogen lamp is used, coupled to a suitable optical device (not shown) enabling a homogenous light density to be produced in the area observed by the camera. In the embodiment shown, the camera observes the light image transmitted through the film 1. This solution is particularly advantageous where it is desired to detect exposure stoppages or objects of significant density on the surface of the film. For objects of a density substantially equal to that of the photographic support, detection by reflection will preferably be used.

The density values measured by the camera are digitized and transmitted to processing means 4 using a microprocessor, in which the density values are compared with a reference profile. The result of this comparison indicates the presence or otherwise of defects on the support examined. During this phase, the aim of which is to detect defects, the film 1 passes at a first speed V1. Typically this speed V1 is approximately 2 to 4 mm/s. This speed obviously depends on what it is desired to detect. The processing means 4 control the device 5 used for driving the film in order to modify the speed thereof. This will be the subject of a more detailed description later.

According to the embodiment shown, the driving device 5 comprises a roller 6 for driving the film, to which is coupled a speed reducer 7 enabling the angular speed of the stepping motor 8 to be reduced. The stepping motor 8 is controlled by an electronic control unit 9 which itself receives its operating instructions from the microprocessor 4. The film comes from an unwinding device 10 comprising a winding-off spool 11 on which the film 1 is wound. The spindle of this spool is driven by a motor 12 via a gearbox 13. The motor 12 is controlled by a variator 14, itself connected to the processing device 4 and to a tension measuring device 15, the function of which is to measure the tension of the film continuously. This tension is compared by the variator 14 with a set value supplied by the device 4. In response to this comparison, the position of the tension measuring device 15 is modified so as to maintain the tension of the film within a given range of values. The film 1, after passing in front of the camera 2, is wound on a winding-on device 16, preferably identical to the winding-off device 10. This solution has the advantage of enabling the device to operate in both directions and facilitating the maintenance thereof.

When the density value measured by the camera 2 indicates, at a point on the support, the presence of a defect (that is to say a positive or negative difference with respect to a reference value), the control device 4 stops the passage of the film and controls the stepping motor so as to reverse the film with respect to the camera 2. The film is reversed by a distance sufficient to position the area observed by the camera upstream of the defect detected. The camera is preferably positioned 30 to 40 µm upstream of the first defect detected so as to take up the mechanical play in the drive system. The device 4 controls the stepping motor so as to drive the film (in the initial direction) at a speed V2 less than the speed V1. This speed is, for example, of the order of 1 mm/s. During this period of passage at speed V2, the density values measured by the camera 2 and digitized are stored line by line by means of any bulk store (for example a hard disk). This process, at the passage speed V2, continues until the area observed by the camera 2 is situated downstream of the last defect detected. At this moment, the processing device 4 controls the electronic unit 9 so as to drive the film 1 at the speed V1 until the following defect is detected. These operations are repeated until the end of the support to be examined or of the area of the support to be examined has been reached.

After that, for example during the periods of loading/unloading of the film, processing is carried out of the data stored during the periods at which the film passes at speed V2. The purpose of this processing is to characterize the defects detected. Within the meaning of the present invention, the term "characterized" means for example a determination of the size of the defects detected, of the shape of the defects, or of the contrast or position of the defects. For example, conventional image processing is carried out. According to a first embodiment, contour extractions are carried out using gradient algorithms, in order, within the file, to detect where the defects are located. It is also possible to use filtering methods in order to eliminate background noise. These processing techniques are known to experts and consequently do not require any additional description. By way of example, the COLOR PC-SCOPE software sold by I2S is used.

Advantageously, in the case of a line-by-line analysis of the support, and in order to improve the speed of the method, the analysis of the data which is carried out for the purpose of detecting the presence of a defect is carried out so that the comparison of the density values relating to the line n with the reference profile mentioned above is performed during the acquisition of the density values of the line n+1. This overlapping analysis reduces the time required for the analysis of a support by approximately one third.

According to a first alternative, the reference profile used for the detection of a defect is variable from one end of the strip to the other in order to compensate for variations in the density of the film over its entire length. For example, a sliding average is effected, that is to say the values obtained are weighted in order to give greater weight to the last values. The reference profile is updated only if the line analyzed does not include any defect.

According to a second alternative, instead of moving the film with respect to the camera, the camera is moved with respect to the support, the important thing being to obtain a relative movement of one with respect to the other so as to position the camera correctly with respect to the defect. This second approach has the advantage of simplifying the film drive mechanisms.

According to a third alternative, each defect detected does not automatically trigger the passage of the film at the reduced speed V2. According to this approach, instead of detecting only the start of a defect, the end thereof is also detected, at the speed V1. This first passage at high speed thus gives an approximate idea of the dimensions and shape of the defect detected. In accordance with this approximate information, it is possible to decide whether a complete analysis of the defect is necessary, in which case the normal procedure of passage at reduced speed is initiated. In the converse case, the procedure continues directly to the following defect. This makes it possible to improve the efficacy of the method according to the requirements of the user.

According to a fourth alternative, an additional processing device is used, connected to the first device 4, and the function of which is to receive the file stored at the speed V2 by the first device 4 in order to be processed therein whilst the first device manages the process of detecting defects on the film at speed V1.

According to yet another alternative, two CCD cameras disposed in succession are used, so that the film first of all passes in front of a first camera, which detects the start and end of the defect at the high speed V1. After detection of the end of the defect and prior to the arrival of the defect in the field of the second camera, the processing means 4 trigger the slowing down of the speed of passage of the strip so that the support passes at the reduced speed V2 in front of the second measuring device, until the defect examined is no longer in the field of observation of the second measuring device, after which the film passage speed V1 is re-established. This solution has the advantage of improving the performance of the method with regard to its speed of execution.

Experts will obviously appreciate that other variations on the embodiments set out above may be introduced without for all that departing from the concept of the present invention. For example, it will be noted that it is possible to use several cameras distributed over the width of the support to be examined, when it is desirable to increase the width inspected whilst keeping an identical resolution, or when, for the same width of the support to be examined, it is desirable to increase the resolution.

I claim:

1. Method for counting and characterizing defects on a photographic support comprising the steps of:

a) transporting in a first direction and at a first speed V1, the support in front of an optical density measuring device so that density profiles of successive transverse lines of said support could be generated;

b) digitizing the density profiles generated by said density measuring device;

c) comparing said density profiles with a reference profile in order to detect the presence of at least one defect and, when such a defect is detected, stopping the movement of the support;

d) moving said support and its associated detected defect relatively to the measuring device so that said defect is located upwards from said measuring device with respect to said first direction;

e) transporting the support and its associated detected defect in front of said measuring device in said first direction and at a second speed V2, less than the first speed V1, until said measuring device has inspected the totality of the detected defect;

f) storing the digitized density profiles of said support during the passage of the support at said second speed V2;

g) repeating steps a) to f) for the remainder of the support;

h) processing the stored density profiles during the periods of passage at speed V2, so as to count and characterize the detected defects.

2. Method according to claim 1 wherein step c) consists of detecting the start and end of the defect by said measuring device at speed V1, and based on the density profiles of the support generated by said measuring device between the start and end of the defect, deciding whether or not to stop the transportation of the support.

3. Method according to claim 1, in which the relative movement of step e) between said measuring means and said support is realized by moving said measuring device.

4. Method according to claim 1, wherein the reference profile is updated only if the line analyzed does not include a defect.

5. Method for counting and characterizing defects on a photographic support comprising the following steps:

a) transporting, in a first direction and at a first speed V1, the support in front of a first and a second optical density measuring devices having respective field of observation so that density profiles of a successive transverse lines of said support could be generated;

b) digitizing the density profiles generated by said density measuring device;

c) comparing said density profiles with a reference profile in order to detect the presence of at least one defect;

d) prior to the arrival of said defect in front of the second measuring device, modifying the speed of transportation of the film to a speed V2, less than V1, until the defect detected by the first measuring device is no longer in the field of observation of the second measuring device;

e) storing the digitized density profiles of said support during the passage of the support at said second speed V2;

f) repeating steps a) to c) for the remainder of the support;

g) transporting the support and its associated detected defect in front of sad measuring device at a second speed V2, less than the first speed V1, until said measuring device has inspected the totality of the detected defect;

h) processing the stored density profiles during the periods of passage at speed V2, so as to count and characterize the detected defects.

* * * * *

UNITED STATES PATENT AND TRADEMARK OFFICE
CERTIFICATE OF CORRECTION

PATENT NO. : 5,641,971
DATED : 24 June 1997
INVENTOR(S) : Thierry Prigent

It is certified that error appears in the above-identified patent and that said Letters Patent is hereby corrected as shown below:

Column 6, line 50      change "sad" to --said--

Signed and Sealed this

Third Day of March, 1998

Attest:

BRUCE LEHMAN

Attesting Officer      Commissioner of Patents and Trademarks